United States Patent [19]

Herzberg

[11] Patent Number: 5,221,609
[45] Date of Patent: Jun. 22, 1993

[54] MOLECULAR GENETIC PROBE, AND METHOD OF FORMING SAME, ASSAY TECHNIQUE AND KIT USING SAID MOLECULAR GENETIC PROBE

[75] Inventor: Max Herzberg, Moshav Sataria, Israel

[73] Assignee: Orgenics Ltd., Israel

[21] Appl. No.: 733,000

[22] Filed: Jul. 18, 1991

Related U.S. Application Data

[63] Continuation of Ser. No. 622,359, Dec. 4, 1990, abandoned, which is a continuation of Ser. No. 925,985, Nov. 3, 1986, abandoned, which is a continuation of Ser. No. 499,440, May 31, 1983, abandoned.

[51] Int. Cl.$^5$ .............................................. C12Q 1/68
[52] U.S. Cl. ............................................ 435/6; 435/5; 435/810; 436/501; 436/63; 436/94; 436/543; 436/544; 436/547; 935/15; 935/77; 935/78; 935/81
[58] Field of Search ................. 435/5, 6, 810, 803; 436/501, 63, 94, 543, 808, 823, 544, 547; 530/387; 935/1, 15, 14, 78, 81

[56] References Cited

U.S. PATENT DOCUMENTS

| 4,139,346 | 2/1979 | Rabbani . | |
|---|---|---|---|
| 4,302,204 | 11/1981 | Wahl et al. . | |
| 4,358,535 | 11/1982 | Falkow et al. . | |
| 4,556,643 | 12/1985 | Paau et al. | 436/504 |
| 4,581,333 | 4/1986 | Kourilsky et al. | 435/188 |
| 4,724,202 | 2/1988 | Dattagupta et al. . | |

FOREIGN PATENT DOCUMENTS

| 0662286 | 10/1982 | European Pat. Off. | 435/5 |
|---|---|---|---|
| 0063879 | 11/1982 | European Pat. Off. . | |
| 649751 | 4/1979 | U.S.S.R. | 435/6 |

OTHER PUBLICATIONS

"Immunological Detection and Quantification of Carcinogen-Modified DNA Components," by Muller, et al., *IARC Scientific Publications* 39: 463-479 (1982).
"A Rapid and Sensitive Immunological Method for In Situ Gene Mapping", by Langer and Ward, *ICN-UCLA Symposium Molecular Cell Biology*, 23, pp. 647-658, (1981).
"Antibodies Specific for Modified Nucleosides: An Immunochemical Approach for the Isolation and Characterization of Nucleic Acids," by Munns and Liszewski, *Progress in Nucleic Acid Research and Mol. Biol.*, 24, 109-165 (1980).
"Reactivity of the Antibodies to DNA Modified by Carcinogen N-Acetoxy-N-acetyl-2-Aminofluorene," by Sage et al. in *Biochemistry*, 18: 1328-1332 (1979).
"An Enzyme-Linked Immunosorbent Assay for Antibodies to Native and Denatured DNA," by Klotz, in *J. of Immunological Methods*, 29: 155-165 (1979).
"Immunological Approaches to DNA Structure Investigation-I. Immunochemical identification of the Product of Cytosine Modification with Bisulfite . . . " by Poverenny, et al. *Molecular Immunology*, 16: 313-316 (1979).
"Immunological Detection of $O^6$-Methylguanine in Alkylated DNA," by Briscoe, et al., *Biochemistry*, 17: 1896-1901 (1978).
"Possible Relevance of O-6-Alkylation of Deoxyguanosine to the Mutagenicity and Carcinogenicity of Nitrosamines and Nitrosamides," by Loveless, *Nature*, 223, 206-207, Jul. 12, 1969.
"Immunological Method of Gene Mapping by In Situ Hybridization," by Langer and Ward, Manuscript (undated).

Primary Examiner—Amelia Burgess Yarbrough
Attorney, Agent, or Firm—Ostrolenk, Faber, Gerb & Soffen

[57] ABSTRACT

A method of assaying for the presence or quantity of a suspect nucleic acid in a suspect sample using a modified genetic probe in combination with an imaging procedure. The probe is modified by addition and provides an easy and very effective technique of modifying a genetic probe preparatory to its use in a kit. The genetic probe is then introduced into contact with DNA or RNA of the suspect sample and permitted to hybridize therewith. A kit for performing an assay using the modified probe is also disclosed.

20 Claims, No Drawings

MOLECULAR GENETIC PROBE, AND METHOD OF FORMING SAME, ASSAY TECHNIQUE AND KIT USING SAID MOLECULAR GENETIC PROBE

This is a continuation of application Ser. No. 07/622,359, filed Dec. 4, 1990, which is a continuation of application Ser. No. 06/925,985, filed on Nov. 3, 1986, which is a continuation of application Ser. No. 06/499,440, filed on May 31, 1983, all abandoned.

BACKGROUND OF THE INVENTION

1. Field of the Invention

The present invention relates to a molecular genetic probe and to a method in which such a probe may be used as part of a DNA- or RNA-based assay technique. More specifically, the molecular genetic probe of the invention finds particular use in assay techniques for determining the presence of a virus gene, a gene sequence, or any gene product, e.g., a code for an enzyme, in a suspect sample containing a suspect nucleic acid wherein the suspect nucleic acid is hybridized to the probe and complexed with a labelling agent whose presence can be quantitatively assayed.

2. Description of Background Research and Discussion of Relevant Materials

The present invention provides a technique for assaying for the presence of a viral gene, a gene sequence, or any gene product, e.g., a code for an enzyme. Such techniques are of obvious diagnostic value and are of particular value in kit form such that they can be performed easily and simply by lab personnel having only limited laboratory skills.

There is a particular demand for such techniques, suitable for kits, which are capable of assaying the presence of a particular pathogen; which are specific, and which operate by sensing the presence of nucleic acid specific to the suspect pathogen. Obviously, it is preferable that such techniques be not only accurate, but that they also require performance of a minimum number of manipulations, both by the laboratory technician, as well as in the manufacture of the reagents used in the assay.

It is desirable that the principle of the assay be based upon detection of DNA, or RNA, since such a technique can be used to detect disease, even when symptoms are not apparent. Such techniques are of particular interest in pathogen assays for use in viral diseases wherein one wishes to determine the presence of a particular virus in particular tissue.

In situ techniques exist for assaying for the presence of particular viral DNA and RNA by using hybridization techniques in which probe DNA capable of hybridizing with the suspect viral DNA is radioisotopically tagged and then added to the test specimen. Standard counting and imaging techniques may then be used to quantitatively assay for the presence and amount of suspect DNA which is present.

Such a technique is broadly disclosed in U.S. Pat. No. 4,358,535 to Falkow et al. in which denatured suspect DNA (or RNA), is contacted with single stranded DNA (RNA) probes which have been labelled. A special denaturation technique is disclosed. The probe is selected to hybridize with the denatured suspect DNA. The screening technique is said to be suitable for use in screening viruses (genital Herpes is specifically mentioned), fungi, protozoa, molds, etc. The label used is generally suggested to be a radionuclide, however the patent mentions that in certain instances it may be feasible to employ antibodies which bind specifically to the probe for detection purposes. In such instances the antibodies themselves are labelled. Labels listed include radioactive labels, and ligands which can serve as a specific binding member to a labelled antibody, fluorescers, chemiluminescers, enzymes, antibodies which can serve as a specific binding pair member for a labelled ligand, and the like.

European Patent Application No. 0062286 discloses a method and test kit for the detection of Hepatitis B virus by nucleic acid hybridization. Once again a hybridization probe is used which can then be assayed by a scintillation counting technique.

Russian Patent 649,751 discloses a method for identifying microorganisms by purifying DNA from a microorganism and hybridizing this DNA to DNA from a reference strain. The DNA is labelled with radioactive thymine.

One drawback of such systems is the necessity of handling radioactive materials during the preparation of the probes which is obviously an unsatisfactory situation. Another disadvantage which appears in these techniques is the relatively sophisticated equipment which is necessary for such an enzymatic process.

Both U.S. Pat. Nos. 4,302,204 (Wahl et al.) and 4,139,346 (Rabbani et al.) also disclose hybridization techniques in which RNA and DNA strands are hybridized with labelled probes as a part of a hybridization technique.

It should be noted that DNA per se is not a satisfactory antigen for purposes of the screening technique which is contemplated. The antibody response of viral DNA is often insufficient and not sufficiently specific to render it usable as an antigen.

The modification of DNA and the use of the modified antigen to elicit an antibody response are known techniques.

An article entitled: "Antibodies Specific for Modified Nucleosides: An Immunochemical Approach for the Isolation and Characterization of Nucleic Acids" by Munns and Liszewski, *Progress in Nucleic Acid Research and Molecular Biology*, Vol. 24, pp. 109-165 (1980), discusses antibodies specific to modified constituents of nucleic acid.

"Immunological Detection of O6-Methylguanine in Alkylated DNA" by Briscoe et al., *Biochemistry*, Vol. 17, pp. 1896-1901 (1978) describes the potential use of antibodies specific for O6-methylguanine which bind directly to alkylated DNA. A radioimmunoassay system employing these antibodies is said to be considered to be a useful approach in detecting O6-methylguanine in DNA treated with certain alkylating agents.

"Reactivity of Antibodies to DNA Modified by the Carcinogen N-Acetoxy-N-acetyl-2-Aminofluorene", by Sage et al., *Biochemistry*, Vol. 18, pp. 1328-1332 (1979) describes the reactivity of antibodies to DNA which were modified by N-Acetoxy-N-acetyl-2-Aminofluorene. These antibodies react with the modified DNA, rather than the unmodified form.

"Possible Relevance of O-6 Alkylation of Deoxyguanosine to the Mutagenicity and Carcinogenicity of Nitrosamines and Nitrosamides", by Loveless, *Nature*, Vol. 223, Jul. 12 (1969) discusses the use of biological alkylating agents such as N-ethyl-N-nitrosourea which modify nucleic acid bases.

Thus, although modification, including ethylation of nucleic acid bases is a recognized phenomenon, the advantages of using this principle in conjunction with hybridization, as part of an efficient assay technique, have not generally previously been appreciated or used to maximum advantage. In fact, while hybridization has been suggested in at least one instance, for use in conjunction with modification in one assay procedure, this procedure does not combine the two techniques to maximum advantage and results in a very cumbersome assay having only limited utility.

Such a technique is seen in European Application S.N. 82301804,9 (published Nov. 13, 1982) which discloses modifying the purine or pyrimidine bases by covalently bonding a moiety consisting of at least three carbon atoms (e.g., biotin) which is capable of forming a detectable complex with a polypeptide when the compound is incorporated into a double stranded RNA, DNA duplex or DNA-RNA hybrid. The polypeptide detectors for the biotin-containing probe may be avidin, streptavidin or an antibiotin immunoglobulin. In particular, the preferred protein for biotin-like probe detection is the antibiotin immunoglobulin. This antibody can be tagged with an enzyme, such as peroxidase. Page 30, line 37 through page 31, lines 1-14 describe the use of an antibody to the biotin constituent. An illustration is provided at page 33 which describes the use of an antibody to detect the biotin or hapten. The IgG-peroxidase example describes an antibody-tagged enzyme detection system. On page 34, lines 25-37 and page 35, lines 1-2, the procedure for utilizing the modified nucleotides to detect the presence of the nucleotide sequences of interest is described. This general protocol can be applied to the detection of nucleic acid sequences of viral, bacterial, fungal or parasitic origins in clinical samples.

As was noted above, this technique is of only limited utility and is extremely cumbersome. Using this technique, nuclease treatment of the template nucleic acid is necessary to nick or open gaps in one of the strands. A biotin substituted base is then inserted into the DNA using polymerase. The modified DNA can only then be complexed with antibiotin which is enzyme tagged to form an antibiotin-enzyme-DNA complex. The double stranded DNA can then be split, with the complexed strand being usable as a probe. Such a technique thus requires that modification occur on DNA in its double stranded form only. The modified single strands can then be used to hybridize only with organisms that contain double stranded nucleic acids, i.e., substances such as single stranded RNA viruses cannot be modified or detected using the approach proposed in this patent application.

Furthermore, the system requires additional reagents such as nuclease and polymerase and the prior synthesis of the biotin base. The use of these substances not only adds to the complexity of the technique but also requires high purity. Also, the use of enzymes which break and then reform the modified nucleic acid chain add to the time and expense involved in manufacturing the kit reagents, again reducing the value of this technique for use in diagnostic kits.

Pages 62-63 of the patent disclose the modification, by addition, of a polynucleotide. Using a mercuric salt, a mercurated derivative is formed. The mercurated derivative is then reacted with a linker arm and a reactive terminal functional group or the modifier itself in the presence of $K_2PdCl_4$. Thus, at least two, if not three, steps are required to perform the modification.

Such a procedure is unsatisfactory because it necessarily requires purification between each step. Also, the use of mercury is a strong disadvantage because it renders the process unusable for double stranded systems due to intercalation. Furthermore, as discussed, a linker arm is necessary because of the position on which the moiety is added. A technique which did not require a linker arm would be much more satisfactory. Yet further, using the technique of the publication, only one addition per base is possible, whereas multiple additions per base may sometimes be desirable.

SUMMARY OF THE INVENTION

It is, therefore, an object of the present invention to provide an assaying or screening technique which is antibody-specific, which is inexpensive, for which the reagents can be easily synthesized, and which has broad utility in assaying nucleic acids from organisms which are both single and double stranded, with little concern for purity.

It is a further object of the invention to provide a technique in which a strong antigen is used, i.e., whereby a strong antibody response is elicited, but which does not nevertheless substantially interfere with hybridization of the probe to the suspect nucleic acid.

Yet another object of the invention is to provide a technique which obviates the use of radionuclides, if one is desirous of minimizing exposure to such materials.

According to yet another objective of the invention, it would be desirable to provide a technique for forming the probe which involves only a one-step addition of the modifying agent, which does not use mercury and allows for addition of more than one modifying agent into a single base on a nucleic acid.

These, and other objects of the invention, are achieved by means of the assaying method of the invention in which the presence or quantity of a suspect nucleic acid in a suspect sample is determined. The invention includes the steps of:

a) contacting the suspect sample with a modified nucleic acid selected such that it will hybridize with the suspect nucleic acid, if it is present, to form a hybridized complex; the modified nucleic acid having been formed by a one-step modification of a base of the nucleic acid;

b) contacting the modified nucleic acid with labelled antibodies selected to complex with at least the modified portion of the modified nucleic acid to form a hybridized complex; and c) measuring for the presence and/or extent of the presence of the labelled antibodies as an indication of the presence or extent of presence of the suspect nucleic acid.

Using such a technique, nucleic acid from organisms containing single, as well as double, stranded DNA and RNA may be assayed, under conditions of less than high purity, which might otherwise be required.

Also, using such a technique a label may be selected which is non-radioactive, thus rendering it easily usable under conditions where one wishes to avoid the handling of radioactive substances. The label may be an enzyme directly or, for example, a second antibody to the first antibody which is itself complexed with an enzyme.

It is a particular advantage of this technique that the DNA or RNA probe itself may be made by direct modification, without enzymatic or other types of nucleic acid manipulation techniques. Specifically, the use of nuclease and polymerase may be avoided.

The probes themselves are either single stranded or double strands which have been at least partially donatured. The primary requirement of the probe is that it be capable of hybridizing with the suspect nucleic acid, when modified.

The particular modification of the DNA or RNA involves modifying nucleic acid bases, and particularly in one preferred embodiment, alkylating the bases. Alkylation may be performed by using an alkylation compound such as alkylnitroso urea, and even more specifically, methyl, ethyl or propyl nitroso urea compounds. In one particularly preferred embodiment the alkylation compound is N-ethyl-nitroso-urea. Quite obviously, other alkylation compounds eliciting similar antibody responses in substantially the same manner may also be used without departing beyond the scope of the invention.

Alkylation of the $O_6$ position of guanidine is preferred although other locations may also be alkylated depending upon the particular compound being used, see Briscoe et al., supra. for one example of an addition modification reaction which may be used according to the invention. The disclosure of this article is incorporated by reference thereto.

According to another embodiment of the invention, modification may take the form of sulfonation. Such a sulfonation technique is disclosed in "Immunochemical Approaches to DNA Structure Investigation-I", by A. M. Poverenny et al., *Molecular Immunology*, Vol. 16, pp. 313-316, Pergamon Press, Ltd., 1979.

Other types of addition reaction modifications, such as nitrosonation, nitrophenylation, etc., may also be used without departing from the scope of the invention.

The inventive technique lends itself readily for use in a kit which tests for the presence of a nucleic acid in a suspect sample. Such a kit includes a supply of modified nucleic acid probes selected such that they will hybridize with the suspect nucleic acid, if it is present, to form a hybridized complex. The modified nucleic acid itself is formed by modification of a base of the probe nucleic acid. Means are provided for contacting the suspect sample with the modified nucleic acid to form the hybridized complex. A supply of antibodies selected to complex with at least the modified portion of the modified nucleic acid is provided. The antibodies are labelled with a labelling agent adapted to signal the presence of the antibody. The kit further includes means for contacting the modified nucleic acid with the labelled antibodies; and means for measuring for the presence and/or extent of the presence of the label as an indication of the presence or extent of presence of the suspect nucleotide.

The probe itself forms one aspect of the invention because of the facility which it provides in an assay such as the inventive assay. Such a probe may be a single or partially denatured double stranded DNA or RNA molecular genetic probe comprising at least one modified base. The base is modified while it is attached to the DNA or RNA in a one-step addition, and without the use of mercury or a linker arm. The probe is further adapted to hybridize with a complementary DNA or RNA strand. Hybridization per se is a known technique and is generally described in numerous publications, see, for example, European Patent Application 82102673.9, published Oct. 13, 1982, page 7. Of course, the probe of the invention acts as an antigen to produce antibodies which find particular use as labelling agents according to the invention. The probe itself may be modified while it is single or double stranded, or when it is partially denatured when a modification technique such as that disclosed herein is used.

DESCRIPTION OF PREFERRED EMBODIMENTS

The instant invention finds particular application in assaying for the presence and/or quantity of nucleic acid from organisms which contain, either single or double stranded nucleic acid, such as DNA and RNA, or their nucleotides. The nucleic acids being assayed according to the invention have at least 10 bases, and preferably at least 50 bases. When assaying for nucleic acids in organisms containing single stranded nucleic acids, hybridization can be performed directly without denaturation.

Prior to assaying cell-contained DNA, the cells must be lysed. To accomplish this, a standard lysing technique is used; or, if desired, a lysing technique of the type described in U.S. Pat. No. 4,358,535 to FALKOW et al., may be used.

An alternative lysing technique according to the invention includes identifying by number colonies on agar, transferring them into separate test tubes containing lysing and denaturing solution, and transferring the lysed and denatured contents onto either nitrocellulose or activated paper.

When assaying for nucleic acid from organisms containing double stranded nucleic acids, a preliminary splitting (denaturation) of the nucleic acid is required so as to render it at least partially single stranded. Such techniques are known and do not form a part of the instant invention. Examples of such techniques are disclosed, for instance, in Gergen, J. P., Stern, R. H. and Wensink, P. C. (1980) Nucleic Acids Res., 7, 2115-2136.

The suspect nucleic acid material may be assayed while suspended in a liquid or when fixed to a suspended or solid substrate, e.g., filter paper or cellulose. The first step of the assay involves hybridizing the suspect nucleic acid with a test probe which is as specific as possible to the substance being assayed. Thus, it is preferred that the probe of the invention be a nucleic acid having at least 10 and preferably at least 50 bases.

The probe itself comprises a single strand, or partially denatured double strand, of nucleic acid, either DNA or RNA, which is either extracted from animal tissue or cloned, both techniques being well known and disclosed, for instance, in Krist et al. (1981), Proc. Natl. Acad. Sci., USA, 78, 2772-2776.

The probe itself is modified, preferably prior to hybridization, by a one-step technique which does not require nicking or enzymatic action on the nucleic acid strand. Instead the probe is modified directly while it is either single or double stranded, or the denatured portion of a partially denatured double strand is modified.

A variety of different modifications may be performed to provide the modified probe. The object of the modification technique is to provide a probe which is an effective antigen, and any modification achieving this aim will be satisfactory provided that it does not interfere with, or substantially hinder the hybridization step in which the probe will be used. Thus, according to the invention the modifying compound may be a compound selected from the group capable of modifying the nucleic acid such that it is substituted with an alkyl group, including alkyl groups, having three or less, or three or more carbon atoms; a sulfono group; a nitroso group, or nitrophenol group. Many other modifying agents may also be used. Specifically, N-methyl nitroso urea, N-ethyl nitroso urea, N-propyl nitroso urea, and N-butyl nitroso urea may be considered for use as alkylating agents, although N-ethyl nitroso urea is preferred. An alkylation technique of this type is known and is disclosed in M. F. Rajewsky et al., Immunological Detection, etc., Carcinogen Fundamental Mechanisms and Environmental Effects, 207-218, 1980, D. Reidel Publishing Co., although it should be remembered that such techniques have not previously been used as part of a hybridization assay. In alkylating with these compounds substitution occurs at various positions on the nucleic acid.

Compounds providing sulfone groups may include bisulphite, or a combination of the same and, for example, O-methylhydroxylamine as in Poverenny et al., supra, which discloses one possible sulfonation technique. Sulfonation occurs as a 6 sulpho 5, 6 dihydro 4-methoxyaminopyrimidon-2 position on the nucleic acid.

Compounds providing nitroso and nitrophenyl groups, as well as any other compounds which modify by addition reaction may also be used.

Once modified by the addition of a compound of the types listed above, the probes are ready for hybridization, and are then contacted with the suspect sample under conditions allowing hybridization to occur.

This contact can be performed using a variety of techniques, such as liquid-liquid contact, as well as contact on a substrate support, etc. Such contact techniques are exemplified by P. S. Thomas, Proc. Natl. Acad. Sci., 1980, 5201-5205.

According to a preferred technique, the suspect DNA or RNA is affixed to a cellulosic support, such as on a piece of filter paper. Specifically, a cellulosic or nitrocellulosic filter support paper may be used which may or may not be porous. One such material is available from New England Nuclear as Gene Screen hybridization transfer membrane. Other support materials such as nonporous plastics may also be used. The probe is then contacted to the support so as to permit it to hybridize with any suspect DNA and/or RNA suspended on the support. This may be accomplished through capillary action by simply applying filter paper to a gel having the probes distributed therein.

After hybridization, and preferably while the hybridized complex is still on the filter paper, the hybridized complex is tagged with a labelling agent which makes an assay possible.

The labelling agent used may be an enzyme, an enzyme-antibody complex, a radioactively tagged antibody or enzyme etc. To avoid the use of radioactive materials, it is preferred that an EIA or like system be used in conjunction, for example, with a colorimetric analysis technique. As in standard EIA techniques, amplification, and the like may be used. One advantage of the invention is that the modified probes are particularly good antigens, and it is preferred for purposes of the invention that the labelling agent used be an antibody, complexed with an enzyme. The antibodies are obtained by standard techniques such as are described by Poverenny et al., supra, or Muller R. Adamkiewicz and M. F. Rajewsky, 10 IARC Scientific Publ, 39 pp. 463-479. The enzymes used may be peroxidase, B galactosidase, hyalyronidase, and alkaline phosphatase as well as others disclosed on pages 52-59 and 61-64 of European Application S.N. 80303405.7, published Jul. 21, 1981; and may be complexed with the antibodies by means of standard techniques.

The invention will now be described by way of example.

EXAMPLE I

Detection of SV 40 sequences in infected cells (This example was actually performed)

a. CV-1 Cells were infected with SV 40 virus and cultivated further for 16 hours. The cells were then trypsinized and diluted in a phosphate buffered saline solution to obtain a final count on the order of 1,000 cells. This suspension was then filtered on nitrocellulose filters and the DNA denatured as described in S. Lavi & S. Etkin, *Carcinogenesis* 2 (1981) 417-423 and in Gall J. G. & Pardue M. L. (1969) *P. NAS* 63 378-383. After preincubation at 67 deg. C. for 4 hours in Denhardt Buffer (Denhardt D. T. "A membrane filter technique for the detection of complementary DNA") (1966) Biochem. Biophys. Res. Com. 23 641-646), concentrated three times, the filters were contacted with the same buffer containing denatured calf thymus DNA (SIGMA) carrier at 100 micrograms/ml concentration as well as a 5 micrograms/ml quantity of SV 40 DNA modified by alkylation with ethyl nitrosourea as indicated below.

b. Alkylation of SV 40 DNA

Pure SV 40 DNA was ethylated using N-ethyl nitrosourea following the procedure described in R. Muller & Rajewsky M. F. (1978) Naturforsch 33 C pp., 897-901, and the DNA, precipitated by ethanol precipitation, was washed twice by reprecipitation and freeze dried. This material constitutes the molecular probe.

c. Antibody formation

Antibodies to ethylated DNA were produced by using calf thymus DNA processed as above for ethylation. Antibody formation was done by repeated injection of ethylated calf thymus DNA (250-1000 micrograms/ml) with the addition of aluminium hydroxide and complete Freund adjuvent to rabbits subcutaneously and in the hind foot. This was repeated and followed by intravenous injection of booster until the titer of antibody obtained was judged sufficient. Alternatively monoclonal antibodies were used.

d. Isolation of specific antibodies

A DNA affinity procedure was used in which antibodies directed against non-modified DNA were bound after 2 hours of incubation. Proteins which were not bound were passed through an affinity column containing ethylated bases and were then further eluted.

e. Demonstration of the SV 40 sequences

Filters prepared as in a) were exposed to probes prepared as in b) for hybridization procedure with the modified probe as described in Lavi et al. (1981). After completion of the hybridization procedure, filters were incubated with a protein solution (10% normal, inactivated serum); washed in saline; and covered with a mixture of anti-ethylated DNA antibodies as in c) for 2 hours at 37 Deg C. The filters were then washed and exposed to commercially available peroxidase conjugated goat-anti rabbit immunoglobulin (Miles-Yeda) and a color reaction developed by standard procedures. The appearance of a staining reaction showed the presence of SV 40 DNA, and its extent showed the amount of such sequences.

The following examples are intended for illustration purposes, although they have not as yet been performed.

EXAMPLE II

Use of modified molecular probes for the identification of specific genes after gel electrophoresis and blotting DNA from *E. Coli* bacteria which have been transformed by a plasmid containing a cloned gene (e.g. globin) is cut by restriction enzymes and processed for electrophoresis and transfer as in Southern E. M. (1975) J. Mol Biol 98, 503–517.

The same plasmid will be processed separately for alkylation or sulfonation as indicated in Example Ib. and will constitute the modified molecular probe.

Hybridization between the modified molecular probe and the blotted DNA fragments can be performed as in Southern E. M. (1975) supra (in which the hybridization material was radioactive).

After completion of hybridization, antibodies as in example 1c) will be used and processed to obtain a color reaction as in example 1c. Only the bands containing part of the globin gene bind with the modified molecular probe and as a consequence with antibodies against it to give rise to a stained reaction. This same procedure can be used for cellular genes and is not restricted to plasmids. Likewise, the procedure is not restricted to prokaryotic cells and can be applied to nucleated cells.

EXAMPLE III

Identification of bacterial colonies

Bacterial colonies on an agar plate are transferred onto nitrocellulose filters or activated paper by blotting and a few "prints" obtained and processed as described by Gall J. G. & Pardue M. L. (1969) Proc. Nat Acad Sci US Washington 63 378–383, for denaturation. Modified molecular probes consisting of DNA fragments specific for one given bacterial strain are made as in Example Ib. Each of the modified molecular probes are applied for hybridization on a separate "print" of the bacterial colonies and processed for antibody reaction as in Example I.

A stained reaction will appear only at the spot corresponding to the bacterial colony possessing a gene complementary to the known modified molecular probe, permitting the direct identification of the nature of the bacterial colony.

EXAMPLE IV

Identification of the presence of a given DNA in a mixture

Friend Leukemia Cells which can be induced to differentiate and produce hemoglobin by addition of DMSO are used in this experiment.

Whole cytoplasmic RNA is isolated at different times after addition of the differentiation factor and fixed on an activated paper as in Alwine J. C., Kemp D, and Stark G (1977) Proc Nat Acad Sci US 74, 5350–5354. A plasmid containing all or part of the globin gene and modified as in example Ib is then used by hybridization against these spots and further processed for antibody reaction and stained reaction as in Example I. The intensity of coloration will be a direct indication of the quantity of globin messenger RNA present in the cytoplasm of these cells at the different stages of differentiation.

EXAMPLE V

Use of double modification to distinguish between two genes

As in Example I cells suspected of containing either Herpes virus type I, Herpes virus type II or of being free of these viral genes are processed onto nitrocellulose filters. These cells can be from a patient (clinical sample) or from cultured cells (research sample). Two modified molecular probes are used.

Herpes I. A plasmid containing a fragment of Herpes I DNA which will not hybridize with Herpes II DNA is obtained and modified by ethyl nitroso urea as in Example I. Antibodies to the modification are raised in rabbits.

Herpes II. A plasmid containing a fragment of Herpes II DNA which will not hybridize with Herpes I DNA is obtained and modified by sulfonation as in Poverenny et al (1979), Molecular Immunology 16 313–316. Antibodies against sulfonated nucleic acid are raised in goats.

A mixture of the two modified molecular probes is then contacted with the suspected sample for hybridization as described in Example Ia.

Two "second" antibodies are now used:

a) Antirabbit immunoglobulin coupled to peroxidase which produces a green dye when the correct substrate is present (ABTS) (22' azino-di-3-ethyl benthiazolin sulfonic acid).

b) Antigoat immunoglobulin coupled to beta galactosidase which gives a blue dye when the correct substrate is present (X gal).

A mixture of the two antibodies is used to determine whether the anti-goat or anti-rabbit attached to the hybridized molecules. The possibilities are differentiated by the color of the final product.

The presence of the green color after complete reaction indicates the presence of the Herpes I genes in the suspected cells.

The presence of a blue color after complete reaction indicates the presence of the Herpes II genes in the suspected cells. The presence of the two colors shows the presence of the two genes. The absence of a stained reaction show that the tissue is free of Herpes I and II genes.

The same kind of determination can be made with more than two modified molecular probes and used to test both body fluids and tissues.

Although the invention has been described with reference to particular means, materials and procedures, it is to be understood that the invention is not limited to the particulars disclosed and extends to all equivalents falling within the scope of the claims.

What is claimed is:

1. A method for assaying for the presence and concentration of a suspect oligonucleotide sequence in a sample by hybridizing the oligonucleotide sequence with a sulfonated oligonucleotide probe comprising the steps of:

providing a sulfonated oligonucleotide probe comprising at least 10 bases including at least one sulfonated cytidine;

forming a hybridized complex between the suspect oligonucleotide sequence and the sulfonated oligonucleotide probe;

contacting the hybridized complex with antibodies to the sulfonated oligonucleotide probe to form an antibody bound complex wherein the antibodies are specific to an oligonucleotide structure including an oligonucleotide sequence containing at least 10 bases including at least one sulfonated cytidine; and measuring the presence and concentration of the antibody bound complex to indicate the presence and concentration of the suspect oligonucleotide sequence.

2. The method according to claim 1 wherein the step of measuring the presence and concentration of the antibody bound complex includes labeling the antibodies specific to an oligonucleotide structure including an oligonucleotide sequence containing at least 10 bases including at least one sulfonated cytidine with an agent adapted to signal the presence of the antibodies.

3. The method according to claim 1 wherein the method for assaying for the presence and concentration of a suspect oligonucleotide sequence in a sample additionally comprises the steps of:

separating the hybridized complex of the suspect oligonucleotide sequence and the sulfonated oligonucleotide probe from unhybridized oligonucleotide sequences and sulfonated oligonucleotide probes to form a first reaction mixture including predominately hybridized complexes;

contacting the hybridized complex with antibodies to the sulfonated oligonucleotide probe to form an antibody bound complex wherein the antibodies are specific to an oligonucleotide structure including an oligonucleotide sequence containing at least 10 bases including at least one sulfonated cytidine;

adding a labeling agent adapted to signal the presence of the antibodies;

removing excess labeled antibody not bound to the hybridized complex to form a second reaction mixture which is essentially free of unreacted labeled antibody; and measuring the presence and concentration of labeled antibody bound complex to indicate the presence and concentration of the suspect oligonucleotide sequence.

4. The method according to claim 1 or claim 3 wherein the step of measuring the presence and concentration of the antibody bound complex includes contacting the antibody bound complex with a second non-radioactively labeled antibody specific to the antibody bound complex.

5. The method according to claim 1 wherein the antibodies are monoclonal antibodies.

6. The method according to claim 1 wherein the suspect oligonucleotide sequence comprises at least 10 bases.

7. The method according to claim 1 wherein the suspect oligonucleotide sequence codes for an enzyme.

8. The method as according to claim 1 wherein the suspect oligonucleotide sequence is a viral DNA oligonucleotide sequence.

9. The method according to claim 1 wherein the suspect oligonucleotide sequence is a viral RNA oligonucleotide sequence.

10. The method according to claim 1 wherein the at least one sulfonated cytidine is sulfonated using a compound selected from the group consisting of bisulfites, O-methyl hydroxylamine and combinations thereof.

11. The method according to claim 4 wherein the non-radioactively labeled antibody specific to the antibody bound complex is labeled with an enzyme selected to provide a color reaction.

12. The method according to claim 11 wherein the enzyme is selected from the group consisting of peroxidase, betagalactosidase, hyaluronidase, and alkaline phosphatase.

13. The method according to claim 1 wherein the suspect oligonucleotide sequence is typically at least one strand of a double stranded nucleic acid sequence and is denatured prior to hybridization with the sulfonated nucleotide probe.

14. The method according to 1 wherein the suspect oligonucleotide is typically a single stranded DNA nucleic acid sequence.

15. The method according to 1 wherein the suspect oligonucleotide is typically a single stranded RNA nucleic acid sequence.

16. The method according to claim 1 wherein the sulfonated nucleotide probe is typically at least one strand of a double stranded DNA nucleic acid and is denatured prior to hybridization with the suspect oligonucleotide sequence.

17. The method according to claim 1 wherein the sulfonated nucleotide probe is typically at least one strand of a double stranded RNA nucleic acid and is denatured prior to hybridization with the suspect oligonucleotide sequence.

18. A kit for assaying for the presence and concentration of a suspect oligonucleotide in a sample comprising:

sulfonated oligonucleotide probes hybridizable to the suspect oligonucleotide in the sample;

means for hybridizing the sulfonated oligonucleotide probes with the suspect oligonucleotide in the sample;

antibodies specific to the sulfonated oligonucleotide probe wherein the antibodies are specific to an oligonucleotide structure including an oligonucleotide sequence containing at least 10 bases including at least one sulfonated cytidine;

means for binding the antibodies to sulfonated oligonucleotide probe;

labeling agents adapted to signal the presence of the antibody; and means for measuring the presence and concentration of the antibody bound complex to indicate the presence and concentration of the suspect oligonucleotide sequence.

19. An antibody to a sulfonated oligonucleotide probe wherein the antibody is specific to an oligonucleotide sequence containing at least one sulfonated cytidine.

20. An antibody according to claim 19 wherein the antibody is a monoclonal antibody.

* * * * *